United States Patent [19]

Hartig et al.

[11] Patent Number: 4,543,427
[45] Date of Patent: Sep. 24, 1985

[54] PREPARATION OF CYCLOHEXANOL AND CYCLOHEXANONE

[75] Inventors: Juergen Hartig, Gruenstadt; Armin Stoessel, Frankenthal; Guenter Herrmann, Heidelberg; Laszlo Marosi, Ludwigshafen, all of Fed. Rep. of Germany

[73] Assignee: BASF Aktiengesellschaft, Fed. Rep. of Germany

[21] Appl. No.: 501,134

[22] Filed: Jun. 6, 1983

[30] Foreign Application Priority Data

Jun. 11, 1982 [DE] Fed. Rep. of Germany ....... 3222144

[51] Int. Cl.<sup>4</sup> ............................................. C07C 45/53
[52] U.S. Cl. .................................... 568/342; 568/798
[58] Field of Search .............. 568/385, 798, 342, 341, 568/311

[56] References Cited

U.S. PATENT DOCUMENTS 2,851,496  9/1958  Cates, Jr. et al. .................... 260/586
3,551,511 12/1970  Aglietti et al. ....................... 568/385
3,557,215  1/1971  Bonnart et al. ...................... 260/586
3,941,845  3/1976  Vaskuil et al. ....................... 568/798
3,987,101 10/1976  Walters et al. ....................... 568/798
4,173,587 11/1979  Wu ..................................... 568/798

FOREIGN PATENT DOCUMENTS 1002754 1/1955  Fed. Rep. of Germany .
1046610 9/1958  Fed. Rep. of Germany .
1193501 3/1959  Fed. Rep. of Germany .
2352378 7/1973  Fed. Rep. of Germany .

OTHER PUBLICATIONS

Minachev et al., "Zeolite Chemistry and Catalysis", AGS, (1971).
Badran et al., Chem. Abst., vol. 93, #81101d.
Rollman, Chem. Abst., vol. 98, #186434w (1983).

Primary Examiner—James H. Reamer
Attorney, Agent, or Firm—Keil & Weinkauf

[57] ABSTRACT

Cyclohexanol and cyclohexanone are prepared by treating cyclohexyl hydroperoxide with a supported catalyst containing from 2 to 30% by weight, calculated as cobalt, of cobalt in oxidic form, at from 30° to 160° C., by a process wherein a zeolite is used as the carrier.

3 Claims, No Drawings

PREPARATION OF CYCLOHEXANOL AND CYCLOHEXANONE

The present invention relates to a process for the preparation of cyclohexanol and cyclohexanone by treating cyclohexyl hydroperoxide with a supported catalyst containing from 2 to 30% by weight, calculated as cobalt, of cobalt in oxidic form, at from 30° to 160° C.

In the oxidation of cyclohexane with air or oxygen under superatmospheric pressure and at elevated temperatures, a mixture of cyclohexanol, cyclohexanone, cyclohexyl hydroperoxide, other peroxides, acids and esters is obtained. To improve the yield, the cyclohexyl hydroperoxide formed is usually converted, under particular conditions, to a mixture of cyclohexanol and cyclohexanone. In many cases, simultaneous decomposition of the resulting cyclohexyl hydroperoxide is effected during the oxidation by the addition of special transition metal salts. Thus, German Pat. No. 1,002,754 describes the oxidation and the deperoxidation with homogeneous solutions of cobalt or chromium salts. Copper and manganese salts also fulfil this purpose, as is evident from German Published Application DAS No. 1,193,501. However, these processes are in need of improvement with regard to the yield. Furthermore, it is necessary to recover the metal salts.

Supported catalysts have also been used for the decomposition of mixtures containing cyclohexyl hydroperoxide. U.S. Pat. No. 2,851,496 describes metals of group 8, e.g. cobalt, on active aluminum oxide, silica gel, carbon or kieselguhr as being suitable catalysts. However, these catalysts are in need of improvement in respect of their service life and their sensitivity to water and to acids.

It is an object of the present invention to provide a catalyst for the decomposition of cyclohexyl hydroperoxide to cyclohexanone and cyclohexanol, which catalyst gives a high yield and high conversion and furthermore has a long service life and is substantially stable to water and acids.

We have found that this object is achieved by a process for the preparation of cyclohexanol and cyclohexanone by treating cyclohexyl hydroperoxide with a supported catalyst containing from 2 to 30% by weight, calculated as cobalt, of cobalt in oxidic form, at from 30° to 160° C., wherein a zeolite is used as the carrier.

The novel process has the advantages that the decomposition of cyclohexyl hydroperoxide to cyclohexanol and cyclohexanone takes place with high conversions and high yields, that the catalyst has a long service life and is substantially stable to water and acids, and that the active catalytic metal is eluted to a smaller extent.

Advantageously, a solution of cyclohexyl hydroperoxide in cyclohexane is employed, a suitable solution containing, for example, from 0.5 to 10% by weight of cyclohexyl hydroperoxide. It is particularly preferable to employ a mixture obtained by oxidation of cyclohexane with molecular oxygen or a gas containing this, e.g. air, in the liquid phase at from 130° to 200° C. and under a pressure of from 5 to 25 bar, in the presence or absence of a catalyst, such as a cobalt salt. Advantageously, the resulting reaction mixture is washed with water or a caustic alkali solution before being subjected to further treatment.

A typical reaction mixture contains, in addition to cyclohexane, from 3 to 7% by weight of cyclohexanone and cyclohexanol and from 0.5 to 3.5% by weight of cyclohexyl hydroperoxide, as well as by-products, such as esters and carboxylic acids with or without water, the amount of the latter, where it is present, being, for example, not more than 2% by weight. Suitable reaction mixtures are obtained, for example, by the process described in German Pat. No. 1,046,610.

The treatment is carried out in the presence of a supported catalyst containing from 2 to 30, in particular from 10 to 25, % by weight, calculated as cobalt, of cobalt in oxidic form, and a zeolite is used as the carrier. The percentages are based on the total material comprising the carrier and the catalytically active metal. Advantageously, an A, X or Y zeolite is used as the carrier. It has also been found to be useful if the catalyst contains from 3 to 16% by weight, calculated as sodium, of sodium in bound form. To achieve better moldability during the preparation of the catalyst, it is advantageous to add to the catalyst material, before the latter is molded, for example not more than 35% by weight of active aluminum oxide or hydroxide, e.g. boehmite, as a binder. In this case, the above percentages are based on the total material comprising the catalytically active metal, the zeolite and the binder. In a particularly preferred catalyst, the catalytically active metal is incorporated into the zeolite.

Suitable catalysts are obtained, for example, by precipitating a cobalt compound from aqueous solution onto one of the above zeolites, the cobalt compound used being capable of conversion to its oxide when heated. Examples of suitable cobalt salts are cobalt nitrate, cobalt sulfate and cobalt acetate. It has proved advantageous to maintain, during precipitation, a pH of from 7.5 to 12, in particular from 8 to 11, by the addition of an aqueous alkali metal hydroxide or carbonate solution. Advantageously, the precipitation is carried out at from 40° to 100° C. The resulting zeolite carrier containing cobalt hydroxide or carbonate is then washed with water, preferably with water containing an alkali, e.g. at pH 8–10. The supported catalyst thus obtained is advantageously dried at from 100° to 150° C., for example for from 2 to 20 hours, and is then sintered at from 200° to 600° C., for example for from 2 to 8 hours. Sintering is advantageously carried out in the presence of molecular oxygen or of a gas containing this, e.g. air.

In addition to the above, preferred method of preparing the catalysts employed, it is also possible to obtain the ready-prepared catalysts by applying cobalt salts by impregnation or spraying, and following this procedure by heating.

It has proved useful, if the catalyst is to be converted to moldings, to add, for example, not more than 35% by weight of boehmite either before or after sintering and to convert the resulting mixture to moldings. It is assumed that cobalt is present in the form of its oxides, although it is not always possible to carry out an X-ray analysis to establish this. It is also possible that partial ion exchange with the zeolite takes place during the preparation.

The treatment of the cyclohexyl hydroperoxide, or of a solution containing this, is carried out at from 30° to 160° C. (particularly good results being obtained at from 80° to 120° C.) and under atmospheric pressure or slightly superatmospheric pressure, for example as employed in the oxidation of cyclohexane, e.g. not more than 20 bar.

The treatment can be carried out batchwise, but in industry the cyclohexyl hydroperoxide-containing solution or reaction mixture is advantageously treated continuously by passing such a solution or mixture over a fixed-bed catalyst. If the activity of the catalyst diminishes after a relatively long operating time, the catalyst can be readily reactivated by treatment with a gas containing molecular oxygen, e.g. air, at from 150° to 500° C.

The cyclohexanol and cyclohexanone obtainable by the process of the invention are useful for the preparation of adipic acid or cyclohexanone oxime, which is a precursor of caprolactam.

The Examples which follow illustrate the process according to the invention.

EXAMPLE 1

(a) Preparation of the catalyst 1,455 g of $Co(NO_3)_2.6H_2O$ are dissolved in 1,000 g of distilled water, and this solution is added to 500 g of zeolite 4A. The aqueous phase is evaporated off in a rotary evaporator under reduced pressure from a water pump and at a water bath temperature of about 95°–100° C., this procedure being carried out until the catalyst is dry. It is then ground, and calcined in a furnace for 3 hours at 300° C. The catalyst then contains 26.6% by weight of Co and 7.8% by weight of Na, and an aqueous suspension of the catalyst has a pH of 9.8 (catalyst I).

To prepare extrudates, the catalyst powder is mixed with boehmite (AlO(OH)), and the mixture is kneaded for half an hour without peptization, and then converted to 4 mm extrudates. These are then calcined once again for 3 hours at 300° C. The ready-prepared catalyst (II) has the following composition: 18% by weight of Co, 5.3% by weight of Na, 23.2% by weight of Al, 0.5% by weight of $NO_3$, remainder Si and O.

(b) Conversion of cyclohexyl hydroperoxide

In a stirred flask provided with an internal thermometer and a reflux condenser, 2 g of the above catalyst powder (I) are stirred for 30 minutes at 80° C. with 100 g of a mixture obtained by oxidizing cyclohexane with air at 145° C. and under 12 bar (composition: 1.81% by weight of cyclohexane, 2.61% by weight of cyclohexanol, 1.48% by weight of cyclohexyl hydroperoxide, remainder cyclohexane and by-products, such as acids and esters). Gas chromatographic analysis of the product gives the following composition: 2.31% by weight of cyclohexane, 3.15% by weight of cyclohexanol, 0.38% by weight of cyclohexyl hydroperoxide, remainder cyclohexane and by-products, such as acids and esters. The yield of cyclohexanone and cyclohexanol is 119% by weight, based on a peroxide conversion of 74% by weight.

COMPARATIVE EXAMPLE 728 g of $Co(NO_3)_2.6H_2O$ are dissolved in 500 ml of distilled water, and 500 ml of 4 mm active carbon extrudates are added to this solution. The supernatant solution is distilled off, and the catalyst is dried at 100° C. in a drying oven. The impregnating process is repeated 5 times, after which the total amount of Co has been applied. The extrudates are dried at from 100° to 110° C., and then calcined in a muffle furnace at 300° C., under an $N_2$ atmosphere. The ready-prepared catalyst contains 32.6% by weight of Co. 2 g of the catalyst are milled, and stirred with 100 g of the above oxidation solution for 30 minutes at 80° C. The peroxide conversion is 94% by weight, and the yield of cyclohexanone and cyclohexanol is only 87% by weight.

EXAMPLE 2

200 ml (150 g) of the catalyst II are introduced into a glass tube which has an internal diameter of 30 mm and a length of 400 mm and is provided with a jacket and an internal thermocouple. The feed mixture is pumped through the catalyst from below, at a constant rate and at 80° C., which is maintained by the heating fluid circulating in the jacket. The feed mixture is obtained from the oxidation of cyclohexane with air, and contains, in addition to cyclohexane, 1.64% by weight of cyclohexanone, 2.40% by weight of cyclohexanol, 1.47% by weight of cyclohexyl hydroperoxide, 0.06% by weight of other peroxides, and 0.9 meq/liter of acids and carboxylates. The reacted mixture is analyzed from time to time. The effective residence time, based on the dead (free) space, is 18.5 minutes.

| Time-on-stream (hours) | Peroxide conversion (%)+ | Cyclohexyl hydroperoxide conversion (%)++ | Yield (%) based on peroxide conversion |
| --- | --- | --- | --- |
| 32 | 91 | 100 | 129 |
| 127 | 90 | 100 | 121 |
| 215 | 90 | 100 | 119 |
| 295 | 90 | 100 | 121 |
| 335 | 90 | 100 | 121 |
| 402 | 90 | 100 | 119 |
| 508 | 90 | 99 | 118 |

+Conversion in %, based on the sum of the peroxides in the reaction mixture
++Conversion of cyclohexyl hydroperoxide After the above time-on-stream, the catalyst is completely unchanged and does not exhibit any scaling or substantial loss of activity.

COMPARATIVE EXAMPLE 2

200 ml (110 g) of the Co/carbon catalyst from Comparative Example 1 are introduced into the above experimental apparatus and brought into contact with the oxidation mixture.

| Time-on-stream (hours) | Peroxide conversion (%)+ | Cyclohexyl hydroperoxide conversion (%) | Yield (%) based on peroxide conversion |
| --- | --- | --- | --- |
| 24 | 98 | 100 | 102 |
| 56 | 96 | 100 | 100 |
| 102 | 91 | 98 | 98 |
| 184 | 85 | 97 | 93 |

EXAMPLE 3

(a) Preparation of the catalyst 50 g of zeolite A are suspended in 2 liters of water, the suspension is heated to 80° C. and the pH is brought to 10.5–11 with sodium hydroxide solution. A solution of 195 g of $Co(NO_3)_2.6H_2O$ in 300 ml of water is added to this suspension in the course of from 1 to 2 hours, the abovementioned pH being maintained by simultaneous addition of a solution of 35 g of sodium hydroxide in 300 ml of water. When the addition is complete, the mixture is brought to 100° C. and then cooled to 60°–70° C., after which the precipitate is filtered off and washed with 1,500 ml of water whose pH has been brought to about 8 by the addition of sodium hydroxide solution. Thereafter, the filter cake is dried for 18 hours at 120° C. and then heated for 3 hours at 300° C. The catalyst thus obtained contains 24.5% by weight of cobalt, 6.8% by weight of sodium and 0.5% by weight of nitrate.

(b) Decomposition of cyclohexyl hydroperoxide

In an autoclave, 100 g of a solution of 2.0% by weight of cyclohexyl hydroperoxide and 2.0% by weight of cyclohexanone in cyclohexane are heated together with 2.0 g of the above catalyst for 30 minutes at 80° C., while stirring. Thereafter, the catalyst is filtered off, washed with cyclohexane and used repeatedly. The filtrate obtained each time is analyzed for cyclohexanone, cyclohexanol and cyclohexyl hydroperoxide. The results are summarized below. After the catalyst has been used for the third time, 0.03 ppm of cobalt is detectable in the product.

| Experiment | Peroxide conversion (%) | Yield (%) based on conversion |
| --- | --- | --- |
| 1 | 68 | 118 |
| 2 | 68 | 117 |
| 3 | 68 | 118 |

We claim:

1. In a process for the preparation of cyclohexanol and cyclohexanone by treating cyclohexyl hydroperoxide with a supported catalyst containing cobalt in oxidic form the improvement which comprises treating the cyclohexyl hydroperoxide at from 30° to 160° C. with a catalyst containing from 2 to 30% by weight, calculated as cobalt, of cobalt in oxidic form and from 3 to 16% by weight, calculated as sodium, of sodium in bound form, supported on a zeolite as the carrier.

2. A process as claimed in claim 1, wherein an A, X or Y zeolite is used as the carrier.

3. A process as claimed in claim 1, wherein the cyclohexyl hydroperoxide-containing mixture used is obtained in the oxidation of cyclohexane with molecular oxygen or a gas containing this.

* * * * *